US00PP30630P2

(12) United States Plant Patent
Nair

(10) Patent No.: US PP30,630 P2
(45) Date of Patent: Jul. 2, 2019

(54) CITRUS PLANT NAMED 'FIRST CANADIAN'

(50) Latin Name: ***Citrus* hybrid**
Varietal Denomination: First Canadian

(71) Applicant: Madhavan M. P. Nair, Grasswood (CA)

(72) Inventor: Madhavan M. P. Nair, Grasswood (CA)

( * ) Notice: Subject to any disclaimer, the term of this patent is extended or adjusted under 35 U.S.C. 154(b) by 0 days.

(21) Appl. No.: 15/932,590

(22) Filed: Mar. 19, 2018

(51) Int. Cl.
*A01H 5/08* (2018.01)

(52) U.S. Cl.
USPC ..... Plt./201

(58) Field of Classification Search
USPC ..... Plt./201
See application file for complete search history.

(56) References Cited

PUBLICATIONS

PLUTO Plant Variety Database Jan. 8, 2019.*

* cited by examiner

*Primary Examiner* — Annette H Para
(74) *Attorney, Agent, or Firm* — Penny J. Aguirre

(57) ABSTRACT

A new cultivar of *Citrus*, 'First Canadian', that is characterized by its low light tolerance when grown in a home windowsill without supplemental lighting in small containers, its fruit that is similar in quality to high quality commercial lemons and essentially seedless, its fruit with a skin thickness of 5 to 6 mm and Brix of 7° to 8° with a tart flavor, its dwarf, bushy plant habit that is ideal for small container windowsill culture in homes and commercial buildings, its ability to grow well and produce an abundance of fruit in hydroculture, its mature fruit with bright yellow skin and a conspicuous style and stigma, its dense flower clusters of 8 to 12 blooms resulting in up to 6 fruits per cluster, and its multiple cycles of blooms and fruit set per year (up to 4 cycles).

3 Drawing Sheets

Botanical classification: *Citrus* hybrid.
Varietal denomination: 'FIRST CANADIAN'.

CROSS REFERENCE TO A RELATED APPLICATION

This application is related to a Canadian plant breeders' rights application filed on Mar. 7, 2011, application No. 11-7213. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Citrus* plant, botanically of hybrid origin and known as *Citrus* 'First Canadian' and will be referred to hereafter by its cultivar name, 'First Canadian'. The new cultivar represents a new dwarf lemon plant that is grown for use in homes under low light conditions.

The new cultivar was derived from an ongoing controlled breeding program conducted by the Inventor in Saskatoon, Saskatchewan, that commenced in 1981. The overall purpose of the breeding program is the creation of a new type of dwarf lemon trees and other hybrid *Citrus* trees that exhibit the fruit quality of commercial varieties that are also Low Light Tolerant [LLT] and can be grown in homes on indoor windowsills in small 6-inch containers with only natural available light.

The new cultivar arose from a cross made in April of 1991 between an unnamed and unpatented proprietary plant from the Inventor's breeding program designated as "CLX-1" (*Citrus medica* x *Citrus limonia*) as the female parent and *Citrus* x *meyeri* (unpatented) as the male parent. 'First Canadian' was selected as a single unique plant amongst the seedlings from the above cross in October 2010.

Asexual propagation of the new cultivar was first accomplished by stem cuttings in Saskatoon Canada, by the Inventor in October of 2010. Asexual propagation by stem cuttings has been determined that the characteristics of this cultivar are stable and are true to type in successive reproductions.

SUMMARY OF THE INVENTION

The following traits have been repeatedly observed and represent the unique characteristics of the new cultivar of *Citrus*. Trials were conducted over many years in Saskatoon, Saskatchewan, Canada.

1. 'First Canadian' exhibits low light tolerance when grown in a home windowsill without supplemental lighting in small containers.
2. 'First Canadian' exhibits fruit that is similar in quality to high quality commercial Lemons and is essentially seedless (an occasionally seed may arise as the plant is apomictic).

3. 'First Canadian' exhibits fruit with a skin thickness of 5 to 6 mm.
4. 'First Canadian' exhibits fruit with a Brix of 7° to 8° with a tart flavor.
5. 'First Canadian' exhibits a dwarf, bushy plant habit that is ideal for small container windowsill culture in homes in cold climates, and can be made into a bonsai tree.
6. 'First Canadian' exhibits good fruit production indoors in homes and commercial buildings where the atmospheric temperature is within 55 to 75° F. and the available light level is of typical of indoor spaces (75-200 μmol/m2/s).
7. 'First Canadian' exhibits the ability to grow well and produce an abundance of fruit in hydroculture (up to 36 fruits per year has been observed).
8. 'First Canadian' exhibits mature fruit with bright yellow skin and a conspicuous style and stigma.
9. 'First Canadian' exhibits dense flower clusters of 8 to 12 flowers resulting in up to 6 fruits per cluster.
10. 'First Canadian' exhibits multiple cycles of blooms and fruit set per year (up to 4 cycles).

The female parent of 'First Canadian', "CLX-1", differs from 'First Canadian' in having fruit that is larger ellipsoid shape in size, blooms and fruits less frequently, and in having less flowers per cluster. The male parent of 'First Canadian', *Citrus* x *meyeri*, differs from 'First Canadian' in having fruit that is smaller in size, epicarp and juice vesicles that are more orange in color, juicier and sweeter with a thinner rind, and in having leaves that are ovate in shape and petioles that lack wings. In addition, *Citrus* x *meyeri*, fails to thrive when grown under low light conditions. 'First Canadian' is unique in its ability to grow and set fruit under low light conditions and the Inventor has not had success in growing any other available cultivars under the same conditions. 'First Canadian' can be compared to the *Citrus* cultivar 'Ponderosa' (not patented), however 'Ponderosa' is grown by home owners outdoors in subtropical climates. 'Ponderosa' differs in having fruit that is more ellipsoid in shape with a nipple present. The fruit is also 3-4 times larger with a rough skin and the tree matures to a much larger size and fails to thrive when grown under low light conditions.

BRIEF DESCRIPTION OF DRAWINGS

The accompanying color photographs illustrate the distinguishing characteristics of the new cultivar 'First Canadian'. The photographs in FIG. 1 and FIG. 2 were taken of plants (and plant parts) 27 years in age as grown in a container (12" in length, 12" in width, 20" in height) in a greenhouse in Saskatoon, Saskatchewan, Canada. The photographs in FIG. 3, FIG. 4, and FIG. 5 were taken of plants (and plant parts) about 2 years in age as grown indoors on a home windowsill in small 6-inch containers in Grasswood, Saskatchewan, Canada.

The photograph in FIG. 1 provides a view of the dwarf habit of a 27 year-old plant of 'First Canadian'.

Figure 1:
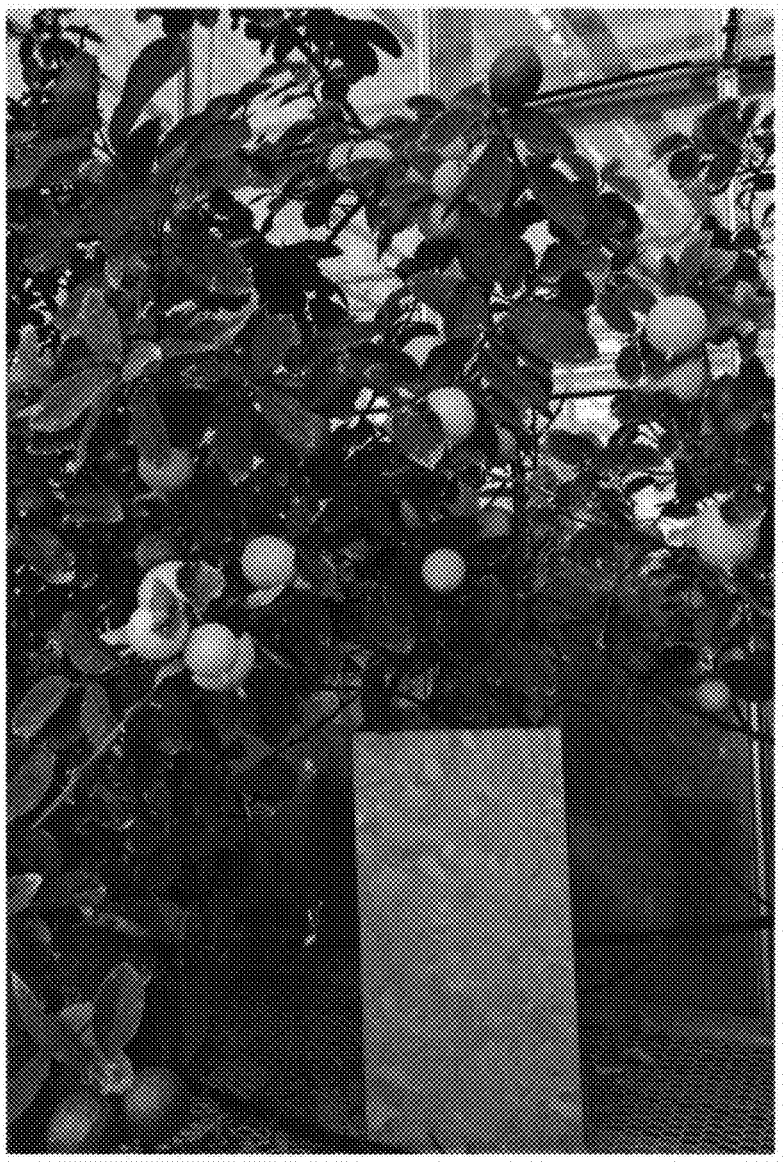
Figure 2:
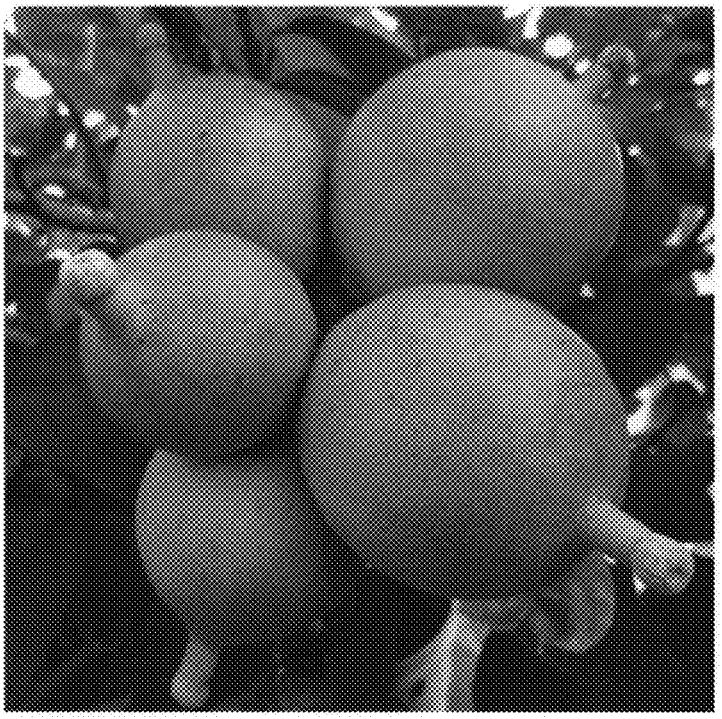

The photograph in FIG. 2 provides a view of maturing fruit of 'First Canadian'.

Figure 3:
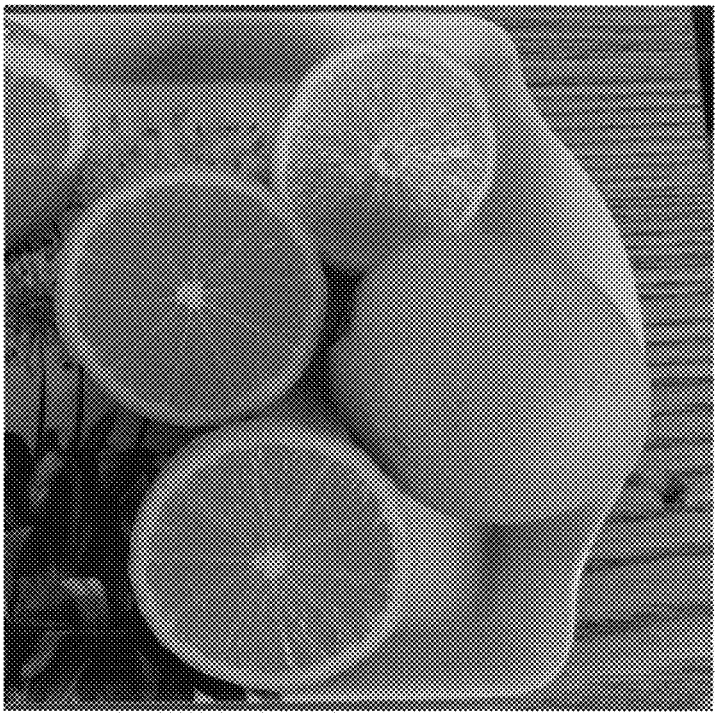

The photograph in FIG. 3 provides a view of a whole fruit and cut fruit of 'First Canadian'.

Figure 4:
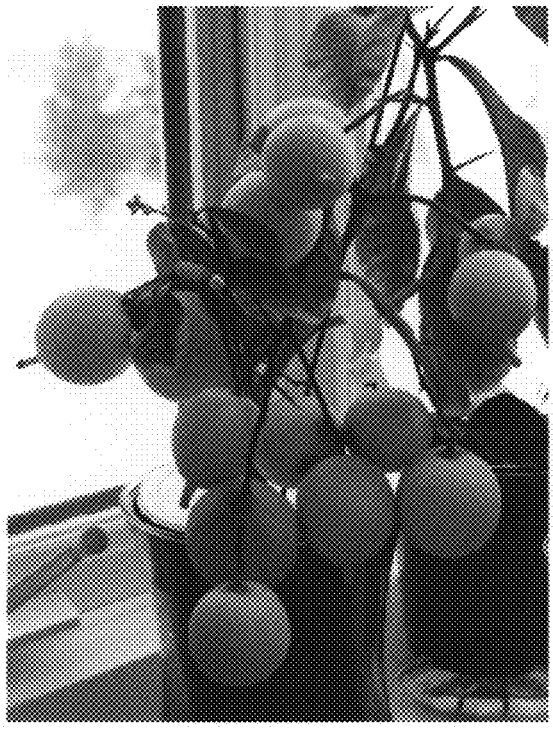

The photograph in FIG. 4 provides a view of a hydroponically grown plant.

Figure 5:
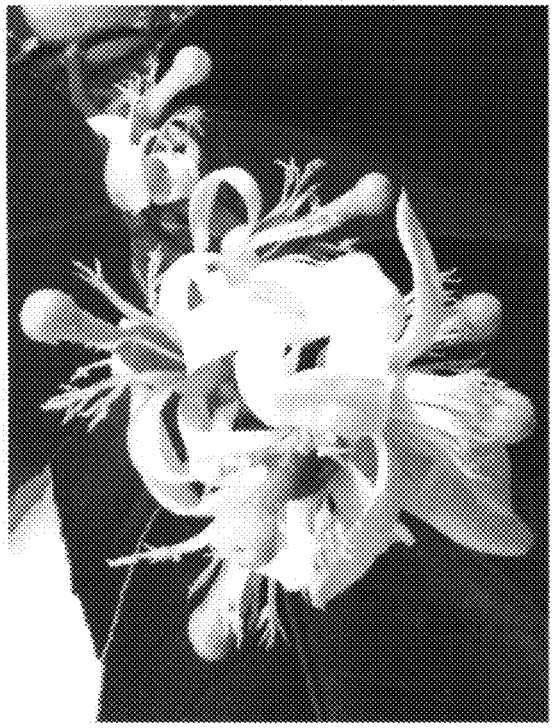

The photograph in FIG. 5 provides a view of an inflorescence.

The colors in the photographs may differ slightly from the color values cited in the detailed botanical description, which accurately describe the colors of the new *Citrus*.

DETAILED BOTANICAL DESCRIPTION OF THE PLANT

The following is a detailed description of 1 to 2-year-old plants of the new cultivar as grown indoors under low light in containers in a greenhouse in Saskatoon, Saskatchewan, Canada. The phenotype has not been observed to be consistent when grown under constant indoor temperature, variable day length, natural reflected light intensity, and proper water and fertility levels. However, the phenotype of the new cultivar may vary with variations in environmental and cultural conditions, as it has not been tested under all possible environmental conditions. The color determination is in accordance with The 2015 Colour Chart of the Royal Horticultural Society, London, England, except where general color terms of ordinary dictionary significance are used.

General description:

*Tree type*.—Sub-tropical bush, evergreen.

*Tree habit*.—Dwarf, upright, rounded, bushy plant habit, can be controlled by pruning for suitable indoor growing area and shape.

*Tree size*.—16 cm in height and 15.4 cm width after 27 years of growth in a relatively small container (12" in length, 12" in width, and 20" in height), outdoor trials in subtropical or tropical environments has not been conducted.

*Growth rate*.—Slow to moderate in a 6-inch container.

*Diseases*.—Although the new cultivar has been observed to be disease free, no susceptibility or resistance to diseases can be claimed as there is no *Citrus* diseases pressure in Canada as they are not naturally grown there.

*Pests*.—No resistance to pests has been observed, control measures may be necessary to treat or avoid insect problems that commonly effect houseplants and greenhouse grown plants.

*Hardiness*.—Grown as an indoor plant only, outdoor trials have not been conducted to date.

*Environmental conditions*.—Performs extremely well in constant temperatures in indoor windows of homes without the addition of any artificial light.

*Propagation*.—Stem cuttings, budding onto rootstock has not been tested.

*Root development*.—Roots initiate in 4 to 6 weeks under mist and become fully rooted in 4 to 6 weeks as a young plant, plants will bloom and set fruit in 4 months to one year depending on the stem location of the stem cuttings (tip or tender shoot cuttings require about one year).

Branch description:

*Trunk description*.—Two main trunks, up to 5 cm in diameter as observed 2.5 cm above soil level on a 27 year-old plant.

*Branching habit*.—Pruning the plant can produce any desirable shape from the main stem.

*Branch strength*.—Adequate to support the heavy load of the fruits, even on a small plant.

*Branch surface*.—Smooth and shiny on new growth, becomes slightly rough and finely ridged as it matures.

*Internode length*.—Average of 2.3 cm.

*Branch color*.—Branches 147B, trunk 199B with thickened bark 199D in roughest and most mature sections.

Description of dormant shoots:

*Branch appearance*.—Flattened to slightly oval on new growth.

*Branch strength*.—Strong and flexible, not brittle.

*Branch size*.—Highly variable in length and 1 to 3 mm in width.

*Branch surface*.—Smooth bark for the first 1 year, then becoming finely ridged.

*Branch internode length*.—Variable depending on the amount of light and season, average of 2 to 4 cm.

*Stem color*.—138A.

*Shoot angle*.—Approximately 45°.

Description of growing shoots:

*Color of shoot*.—140A, mature shoot a color between 138A and 137B.

*Shoot size*.—Highly variable in length and an average of 3 mm in width. hoot

*Shoot surface*.—Glabrous.

Foliage description:

*Leaf orientation*.—Upward to outward with aspect slightly cupped inward (influenced by light source).

*Leaf division*.—Simple.

*Leaf shape*.—Elliptic.

*Leaf arrangement*.—Irregular.

*Leaf size*.—Average of 11 cm in length and 5.5 to 6.5 cm in width (leaves are smaller towards the tip and under higher light).

*Leaf apex*.—Acuminate.

*Leaf base*.—Cuneate.

*Leaf surface*.—Glabrous and satiny on both surfaces, speckled with minute translucent oil glands.

*Leaf texture*.—Thick and leathery.

*Leaf margin*.—Crenulate at 3 to 5 mm intervals.

*Leaf color*.—Upper surface emerging leaves 138C, upper surface mature leaves 138A, lower surface emerging leaves 138D, lower surface mature leaves 138A.

*Leaf venation*.—Pinnate, upper surface; 138A in color, lower surface; prominently raised main vein and slightly raised lateral veins, 138A in color.

*Petiole*.—Slightly winged near leaf base, average of 1.3 to 1.5 cm in length, 2 mm in diameter, wings 1 mm in width, 138A in color, glabrous surface.

*Durability of foliage to stress*.—Returns from wilting with no damage.

*Thorns*.—Attachment is superior to leaf petiole and lateral to bud, linear in shape, average of 1 to 4 cm in length, 0.5 to 2 mm in diameter, color 138A at base and 170B at apex.

Flower description:

*Flowering period*.—Average of every 90 to 120 days, will bloom indoors up to 4 times per year, cuttings will bloom immediately to 3 to 4 months or later depending on the stem location where the cuttings were taken.

*Number of flowers*.—Average of 6 to 12 per node.

*Inflorescence type*.—Clusters borne on axillary nodes.

*Inflorescence size*.—Average cluster is about 5 cm in diameter, depending upon the number of blooms.

*Flower buds*.—Oblong in shape, NN155B in color, an average of 2 cm in length and 5 to 7 mm in diameter, glabrous surface.

*Flower size*.—When fully opened, average of 6 cm in diameter, 2.5 to 3 cm in depth.

*Flower fragrance*.—Mildly sweet, lemongrass-like.

*Flower aspect*.—Upright and outward.

*Petals*.—5 per flower, un-fused, elliptic in shape and recurved, acute apex, truncate base, entire margin, about 1.8 cm in length and 5 mm in width, color of upper and lower surface NN155B and mature to NN155D, surface is satiny and glabrous, thick substance, readily shed.

*Calyx*.—Fused sepals, circular, cupped around ovary, 5 to 7 mm in diameter, an average of 2 mm in depth, waxy surface.

*Peduncle*.—138A in color, 2 to 4 cm in length and an average of 1.5 mm in width, waxy surface.

*Pedicel*.—An average of 2 mm in width and length, 138A in color, waxy surface.

Reproductive organs:

*Hypogynium*.—Small and barely visible to the naked eye.

*Gynoecium*.—Pistil; 1, 2 to 2.2 cm in length, stigma; 5 mm in diameter, 150C in color, style; 9 to 1.2 cm in length and 2 to 2.5 mm in width, 145C in color, ovary; 8 mm in width, 1.2 cm in length, 150D in color.

*Androecium*.—Stamens; average of 24, filaments; 8 mm in length, fused into upright ring, 155C in color, anther; spear shaped, 1.5 to 2 mm in length, 7A in color, pollen; moderate in quantity, 20B in color.

Fruit description:

*Fruit harvest*.—Present year around in various stages of development are present, on average, it flowers every 3 months for 4 crops per year.

*Fruit type*.—Hesperidium.

*Fruit size*.—5 to 6 cm in diameter, 6 to 6.5 cm in length.

*Fruit shape*.—Spheroid with an extended style and stigma 5 to 7 mm in length.

*Fruit symmetry*.—Roughly symmetrical from left to right hemisphere and top to bottom hemisphere with an extended style with stigma at the distal end of the fruit, truncated at the proximal end (the base of the fruit).

*Fruit flavor*.—Tart.

*Fruit weight*.—Average of 110 grams.

*Fruit aroma*.—Strong lemon scented.

*Fruit flesh color*.—4B with endocarp partitions 155B.

*Color of axis*.—155B.

*Flesh texture*.—Glossy, juicy.

*Navel presence*.—None, instead of a navel, a style 5 to 7 mm in length with a stigma present on the majority of fruits at maturity.

*Skin (rind)*.—5 to 6 mm in thickness, outer layer pitted, glossy, brilliant yellow epicarp with oil glands (medium pits), 4B in color, average 2 to 3 mm in thickness, inner surface (mesocarp or albedo); fibrous, 155B in color, average of 3 mm in thickness.

*Fruit segments*.—10 to 12, an average of 4.5 to 5 cm in length and 1.5 to 2.25 cm in width.

*Fruit brix*.—Typically 7° to 8°.

*Fruit set*.—Heavy, best to thin out the flowers when blooming.

*Seed*.—Seedless (an occasionally seed may arise as the plant is apomictic).

*Cropping frequency*.—Year around, fruits need to be picked prevent the fruiting branch from drying up.

*Juice production*.—An average of 35 to 40 ml per fruit.

*Fruit keeping quality*.—2 to 3 weeks at room temperatures before rind begins to mummify and fruit volume begins to shrink from dehydration, 6 to 8 weeks if refrigerated with humidity control, the fruit will remain juicy for many months on the plant until harvested but will eventually dehydrate.

*Fruit shipping quality*.—The fruit is thick skinned and suitable packing materials may be used to transport.

*Fruit use*.—Home use, primarily for fresh consumption, juice and processing into pickles, or rind for candy making, not intended for commercial juicing.

It is claimed:

1. A new and distinct variety of *Citrus* tree named 'First Canadian' as described and illustrated herein.

* * * * *